US012127817B2

(12) United States Patent
Salcido et al.

(10) Patent No.: US 12,127,817 B2
(45) Date of Patent: Oct. 29, 2024

(54) SYSTEMS AND METHODS FOR MITIGATING THE SPREAD OF INFECTIOUS DISEASES

(71) Applicant: Electronic Caregiver, Inc., Las Cruces, NM (US)

(72) Inventors: Roberto Abel Salcido, El Paso, TX (US); Anthony Dohrmann, El Paso, TX (US); Flor Ortiz, El Paso, TX (US); Ivan Nieto, Columbus, NM (US); Audra Lamoreaux, Las Cruces, NM (US); Timothy Washburn, Las Cruces, NM (US); David W. Keeley, Frisco, TX (US); Mark Francis, Portland, OR (US)

(73) Assignee: Electronic Caregiver, Inc., Las Cruces, NM (US)

( * ) Notice: Subject to any disclaimer, the term of this patent is extended or adjusted under 35 U.S.C. 154(b) by 729 days.

(21) Appl. No.: 17/183,118

(22) Filed: Feb. 23, 2021

(65) Prior Publication Data
US 2022/0022760 A1    Jan. 27, 2022

Related U.S. Application Data

(60) Provisional application No. 63/067,757, filed on Aug. 19, 2020, provisional application No. 63/055,236, filed on Jul. 22, 2020.

(51) Int. Cl.
*G16H 10/20*    (2018.01)
*A61B 5/00*    (2006.01)
(Continued)

(52) U.S. Cl.
CPC ........ *A61B 5/02055* (2013.01); *A61B 5/0022* (2013.01); *A61B 5/14532* (2013.01);
(Continued)

(58) Field of Classification Search
CPC ......... G16H 50/20; G16H 50/80; G16H 10/20
See application file for complete search history.

(56) References Cited

U.S. PATENT DOCUMENTS

| 5,211,642 A | 5/1993 | Clendenning |
| 5,475,953 A | 12/1995 | Greenfield |

(Continued)

FOREIGN PATENT DOCUMENTS

| CN | 104361321 A | 2/2015 |
| CN | 106056035 A | 10/2016 |

(Continued)

OTHER PUBLICATIONS

"International Search Report" and "Written Opinion of the International Searching Authority," Patent Cooperation Treaty Application No. PCT/US2018/057814, Jan. 11, 2019, 9 pages.
(Continued)

*Primary Examiner* — Jay M. Patel
(74) *Attorney, Agent, or Firm* — Carr & Ferrell LLP

(57) ABSTRACT

Exemplary methods are provided for real-time assessment of a potential risk of an infectious disease, including receiving a predetermined acceptable range for an aspect of a human user's physiological measurement data, receiving a predetermined acceptable answer for a survey response question, securely receiving an aspect of the human user's physiological measurement data, determining if the aspect of the human user's physiological measurement data is within the predetermined acceptable range, if the aspect of the human user's physiological measurement data is within the predetermined acceptable range, transmitting to the human user a survey comprising a question, if the aspect of the human user's physiological measurement data is not within the predetermined acceptable range, transmitting an active alert and not providing the human user with the survey comprising a question, and if the human user fails to transmit an (Continued)

acceptable answer to the survey comprising the question, transmitting an active alert.

20 Claims, 17 Drawing Sheets

(51) Int. Cl.
| | |
|---|---|
| *A61B 5/0205* | (2006.01) |
| *A61B 5/145* | (2006.01) |
| *G06F 21/60* | (2013.01) |
| *G07C 9/00* | (2020.01) |
| *G07C 9/23* | (2020.01) |
| *G07C 9/25* | (2020.01) |
| *G16H 50/20* | (2018.01) |
| *G16H 50/80* | (2018.01) |
| *A61B 5/021* | (2006.01) |
| *A61B 5/091* | (2006.01) |

(52) U.S. Cl.
CPC ............ *A61B 5/14542* (2013.01); *A61B 5/41* (2013.01); *A61B 5/7267* (2013.01); *A61B 5/7275* (2013.01); *A61B 5/742* (2013.01); *A61B 5/746* (2013.01); *A61B 5/7475* (2013.01); *G06F 21/602* (2013.01); *G07C 9/00563* (2013.01); *G07C 9/23* (2020.01); *G07C 9/25* (2020.01); *G16H 10/20* (2018.01); *G16H 50/20* (2018.01); *G16H 50/80* (2018.01); *A61B 5/021* (2013.01); *A61B 5/091* (2013.01)

(56) References Cited

U.S. PATENT DOCUMENTS

| | | |
|---|---|---|
| 6,665,647 B1 | 12/2003 | Haudenschild |
| 7,233,872 B2 | 6/2007 | Shibasaki et al. |
| 7,445,086 B1 | 11/2008 | Sizemore |
| 7,612,681 B2 | 11/2009 | Azzaro et al. |
| 7,971,141 B1 | 6/2011 | Quinn et al. |
| 8,206,325 B1 | 6/2012 | Najafi et al. |
| 8,771,206 B2 | 7/2014 | Gettelman et al. |
| 9,317,916 B1 | 4/2016 | Hanina et al. |
| 9,591,996 B2 | 3/2017 | Chang et al. |
| 9,972,187 B1 | 5/2018 | Srinivasan et al. |
| 10,387,963 B1 | 8/2019 | Leise et al. |
| 10,628,635 B1 | 4/2020 | Carpenter, II et al. |
| 10,813,572 B2 | 10/2020 | Dohrmann et al. |
| 11,113,943 B2 | 9/2021 | Wright et al. |
| 11,213,224 B2 | 1/2022 | Dohrmann et al. |
| 2002/0062342 A1 | 5/2002 | Sidles |
| 2002/0196944 A1 | 12/2002 | Davis et al. |
| 2004/0109470 A1 | 6/2004 | Derechin et al. |
| 2005/0035862 A1 | 2/2005 | Wildman et al. |
| 2005/0055942 A1 | 3/2005 | Maelzer et al. |
| 2007/0238936 A1 | 10/2007 | Becker |
| 2008/0010293 A1 | 1/2008 | Zpevak et al. |
| 2008/0186189 A1 | 8/2008 | Azzaro et al. |
| 2009/0094285 A1 | 4/2009 | Mackle et al. |
| 2010/0124737 A1 | 5/2010 | Panzer |
| 2011/0092779 A1* | 4/2011 | Chang ..................... A61B 5/00 600/301 |
| 2011/0126207 A1 | 5/2011 | Wipfel et al. |
| 2011/0145018 A1 | 6/2011 | Fotsch et al. |
| 2011/0232708 A1 | 9/2011 | Kemp |
| 2012/0025989 A1 | 2/2012 | Cuddihy et al. |
| 2012/0075464 A1 | 3/2012 | Derenne et al. |
| 2012/0120184 A1 | 5/2012 | Fornell et al. |
| 2012/0121849 A1 | 5/2012 | Nojima |
| 2012/0154582 A1 | 6/2012 | Johnson et al. |
| 2012/0165618 A1 | 6/2012 | Algoo et al. |
| 2012/0179067 A1 | 7/2012 | Wekell |
| 2012/0179916 A1 | 7/2012 | Staker et al. |
| 2012/0229634 A1 | 9/2012 | Laett et al. |
| 2012/0253233 A1 | 10/2012 | Greene et al. |
| 2013/0000228 A1 | 1/2013 | Ovaert |
| 2013/0127620 A1 | 5/2013 | Siebers et al. |
| 2013/0145449 A1 | 6/2013 | Busser et al. |
| 2013/0167025 A1 | 6/2013 | Patri et al. |
| 2013/0204545 A1 | 8/2013 | Solinsky |
| 2013/0212501 A1 | 8/2013 | Anderson et al. |
| 2013/0237395 A1 | 9/2013 | Hjelt et al. |
| 2013/0289449 A1 | 10/2013 | Stone et al. |
| 2013/0303860 A1 | 11/2013 | Bender et al. |
| 2014/0128691 A1 | 5/2014 | Olivier |
| 2014/0142963 A1* | 5/2014 | Hill ........................ G16H 10/60 705/2 |
| 2014/0148733 A1 | 5/2014 | Stone et al. |
| 2014/0171039 A1 | 6/2014 | Bjontegard |
| 2014/0171834 A1 | 6/2014 | DeGoede et al. |
| 2014/0232600 A1 | 8/2014 | Larose et al. |
| 2014/0243686 A1 | 8/2014 | Kimmel |
| 2014/0257852 A1 | 9/2014 | Walker et al. |
| 2014/0267582 A1 | 9/2014 | Beutter et al. |
| 2014/0278605 A1 | 9/2014 | Borucki et al. |
| 2014/0330172 A1 | 11/2014 | Jovanov et al. |
| 2014/0337048 A1 | 11/2014 | Brown et al. |
| 2014/0358828 A1 | 12/2014 | Phillipps et al. |
| 2014/0368601 A1 | 12/2014 | deCharms |
| 2015/0019250 A1 | 1/2015 | Goodman et al. |
| 2015/0109442 A1 | 4/2015 | Derenne et al. |
| 2015/0169835 A1 | 6/2015 | Hamdan et al. |
| 2015/0359467 A1 | 12/2015 | Tran |
| 2016/0026354 A1 | 1/2016 | McIntosh et al. |
| 2016/0117470 A1 | 4/2016 | Welsh et al. |
| 2016/0154977 A1 | 6/2016 | Jagadish et al. |
| 2016/0217264 A1 | 7/2016 | Sanford |
| 2016/0253890 A1 | 9/2016 | Rabinowitz et al. |
| 2016/0267327 A1 | 9/2016 | Franz et al. |
| 2016/0314255 A1 | 10/2016 | Cook et al. |
| 2017/0000387 A1 | 1/2017 | Forth et al. |
| 2017/0000422 A1 | 1/2017 | Moturu et al. |
| 2017/0024531 A1* | 1/2017 | Malaviya ............... G16H 50/30 |
| 2017/0055917 A1 | 3/2017 | Stone et al. |
| 2017/0140631 A1 | 5/2017 | Pietrocola et al. |
| 2017/0147154 A1 | 5/2017 | Steiner et al. |
| 2017/0192950 A1 | 7/2017 | Gaither et al. |
| 2017/0193163 A1 | 7/2017 | Melle et al. |
| 2017/0197115 A1 | 7/2017 | Cook et al. |
| 2017/0213145 A1 | 7/2017 | Pathak et al. |
| 2017/0273601 A1 | 9/2017 | Wang et al. |
| 2017/0300652 A1* | 10/2017 | Strobridge ............. G16H 80/00 |
| 2017/0337274 A1 | 11/2017 | Ly et al. |
| 2017/0344706 A1 | 11/2017 | Torres et al. |
| 2017/0344832 A1 | 11/2017 | Leung et al. |
| 2018/0075558 A1 | 3/2018 | Hill, Sr. et al. |
| 2018/0165938 A1 | 6/2018 | Honda et al. |
| 2018/0182472 A1 | 6/2018 | Preston et al. |
| 2018/0189756 A1 | 7/2018 | Purves et al. |
| 2018/0322405 A1 | 11/2018 | Fadell et al. |
| 2018/0360349 A9 | 12/2018 | Dohrmann et al. |
| 2018/0368780 A1 | 12/2018 | Bruno et al. |
| 2019/0029900 A1 | 1/2019 | Walton et al. |
| 2019/0042700 A1 | 2/2019 | Alotaibi |
| 2019/0057320 A1 | 2/2019 | Docherty et al. |
| 2019/0090786 A1 | 3/2019 | Kim et al. |
| 2019/0116212 A1 | 4/2019 | Spinella-Mamo |
| 2019/0130110 A1 | 5/2019 | Lee et al. |
| 2019/0164015 A1 | 5/2019 | Jones, Jr. et al. |
| 2019/0196888 A1 | 6/2019 | Anderson et al. |
| 2019/0220727 A1 | 7/2019 | Dohrmann et al. |
| 2019/0259475 A1 | 8/2019 | Dohrmann et al. |
| 2019/0282130 A1 | 9/2019 | Dohrmann et al. |
| 2019/0286942 A1 | 9/2019 | Abhiram et al. |
| 2019/0311792 A1 | 10/2019 | Dohrmann et al. |
| 2019/0318165 A1 | 10/2019 | Shah et al. |
| 2019/0385749 A1 | 12/2019 | Dohrmann et al. |
| 2020/0101969 A1 | 4/2020 | Natroshvili et al. |
| 2020/0251220 A1 | 8/2020 | Chasko |
| 2020/0357256 A1 | 11/2020 | Wright et al. |
| 2021/0007631 A1 | 1/2021 | Dohrmann et al. |
| 2021/0049238 A1* | 2/2021 | Vaughn ................. G06N 20/00 |

(56) References Cited

U.S. PATENT DOCUMENTS

| | | | |
|---|---|---|---|
| 2021/0273962 | A1 | 9/2021 | Dohrmann et al. |
| 2021/0358202 | A1 | 11/2021 | Tveito et al. |
| 2021/0375084 | A1* | 12/2021 | Aubrey .................. G07C 9/27 |
| 2021/0398410 | A1 | 12/2021 | Wright et al. |

FOREIGN PATENT DOCUMENTS

| | | | |
|---|---|---|---|
| CN | 107411515 | A | 12/2017 |
| CN | 111801645 | A | 10/2020 |
| CN | 111801939 | A | 10/2020 |
| CN | 111867467 | A | 10/2020 |
| EP | 3740856 | A1 | 11/2020 |
| EP | 3756344 | A1 | 12/2020 |
| EP | 3768164 | A1 | 1/2021 |
| EP | 3773174 | A1 | 2/2021 |
| EP | 3815108 | A1 | 5/2021 |
| EP | 3920797 | A1 | 12/2021 |
| IN | 202027033318 | A | 10/2020 |
| IN | 202027035634 | A | 10/2020 |
| JP | 2002304362 | A | 10/2002 |
| JP | 2005228305 | A | 8/2005 |
| JP | 2016525383 | A | 8/2016 |
| KR | 1020160040078 | A | 4/2016 |
| KR | 1020200105519 | A | 9/2020 |
| KR | 1020200121832 | A | 10/2020 |
| KR | 1020200130713 | A | 11/2020 |
| WO | WO2000005639 | A2 | 2/2000 |
| WO | WO2014043757 | A1 | 3/2014 |
| WO | WO2018032089 | A1 | 2/2018 |
| WO | WO2019143397 | A1 | 7/2019 |
| WO | WO2019164585 | A1 | 8/2019 |
| WO | WO2019182792 | A1 | 9/2019 |
| WO | WO2019199549 | A1 | 10/2019 |
| WO | WO2019245713 | A1 | 12/2019 |
| WO | WO2020163180 | A1 | 8/2020 |
| WO | WO2020227303 | A1 | 11/2020 |

OTHER PUBLICATIONS

"International Search Report" and "Written Opinion of the International Searching Authority," Patent Cooperation Treaty Application No. PCT/US2018/068210, Apr. 12, 2019, 9 pages.
"International Search Report" and "Written Opinion of the International Searching Authority," Patent Cooperation Treaty Application No. PCT/US2019/021678, May 24, 2019, 12 pages.
"International Search Report" and "Written Opinion of the International Searching Authority," Patent Cooperation Treaty Application No. PCT/US2019/025652, Jul. 18, 2019, 11 pages.
"International Search Report" and "Written Opinion of the International Searching Authority," Patent Cooperation Treaty Application No. PCT/US2019/034206, Aug. 1, 2019, 11 pages.
Rosen et al., "Slipping and Tripping: Fall Injuries in Adults Associated with Rugs and Carpets," Journal of Injury & Violence Research, 5(1), (2013), pp. 61-69.
Bajaj, Prateek, "Reinforcement Learning", GeeksForGeeks.org [online], [retrieved on Mar. 4, 2020], Retrieved from the Internet :<URL:https://www.geeksforgeeks.org/what-is-reinforcement-learning/>, 7 pages.
Kung-Hsiang, Huang (Steeve), "Introduction to Various RL Algorithms. Part I (Q-Learning, Sarsa, DQN, DDPG)", Towards Data Science, [online], [retrieved on Mar. 4, 2020], Retrieved from the Internet:<URL:https://towardsdatascience.com/introduction-to-various-reinforcement-learning-algorithms-i-q-learning-sarsa-dqn-ddpg-72a5e0cb6287>, 5 pages.
Bellemare et al., A Distributional Perspective on Reinforcement Learning:, Proceedings of the 34th International Conference on Machine Learning, Sydney, Australia, Jul. 21, 2017, 19 pages.
Friston et al., "Reinforcement Learning or Active Inference?" Jul. 29, 2009, [online], [retrieved on Mar. 4, 2020], Retrieved from the Internet:<URL:https://doi.org/10.1371/journal.pone.0006421 PLoS ONE 4(7): e6421>, 13 pages.
Zhang et al., "DQ Scheduler: Deep Reinforcement Learning Based Controller Synchronization in Distributed SDN" ICC 2019—2019 IEEE International Conference on Communications (ICC), Shanghai, China, doi: 10.1109/ICC.2019.8761183, pp. 1-7.
"International Search Report" and "Written Opinion of the International Searching Authority," Patent Cooperation Treaty Application No. PCT/US2020/031486, Aug. 3, 2020, 7 pages.
"International Search Report" and "Written Opinion of the International Searching Authority," Patent Cooperation Treaty Application No. PCT/US2020/016248, May 11, 2020, 7 pages.
"Office Action", Australia Patent Application No. 2019240484, Nov. 13, 2020, 4 pages.
"Office Action", Australia Patent Application No. 2018403182, Feb. 5, 2021, 5 pages.
"Office Action", Australia Patent Application No. 2018409860, Feb. 10, 2021, 4 pages.
Leber, Jessica, "The Avatar Will See You Now", MIT Technology Review, Sep. 17, 2013, 4 pages.
"Office Action", India Patent Application No. 202027035634, Jun. 30, 2021, 10 pages.
"Office Action", India Patent Application No. 202027033121, Jul. 29, 2021, 7 pages.
"Office Action", Canada Patent Application No. 3088396, Aug. 6, 2021, 7 pages.
"Office Action", China Patent Application No. 201880089608.2, Aug. 3, 2021, 8 pages.
"Office Action", Japan Patent Application No. 2020-543924, Jul. 27, 2021, 3 pages [6 pages with translation].
"Office Action", Australia Patent Application No. 2019240484, Aug. 2, 2021, 3 pages.
"Office Action", Canada Patent Application No. 3089312, Aug. 19, 2021, 3 pages.
"Extended European Search Report", European Patent Application No. 18901139.8, Sep. 9, 2021, 6 pages.
"Office Action", Canada Patent Application No. 3091957, Sep. 14, 2021, 4 pages.
"Office Action", Japan Patent Application No. 2020-540382, Aug. 24, 2021, 7 pages [13 pages with translation].
"Extended European Search Report", European Patent Application No. 18907032.9, Oct. 15, 2021, 12 pages.
Marston et al., "The design of a purpose-built exergame for fall prediction and prevention for older people", European Review of Aging and Physical Activity 12:13, <URL:https://eurapa.biomedcentral.com/track/pdf/10.1186/s11556-015-0157-4.pdf>, Dec. 8, 2015, 12 pages.
Ejupi et al., "Kinect-Based Five-Times-Sit-to-Stand Test for Clinical and In-Home Assessment of Fall Risk in Older People", Gerontology (vol. 62), (May 28, 2015), <URL:https://www.karger.com/Article/PDF/381804>, May 28, 2015, 7 pages.
Festl et al., "iStoppFalls: A Tutorial Concept and prototype Contents", <URL:https://hcisiegen.de/wp-uploads/2014/05/isCtutorialdoku.pdf>, Mar. 30, 2013, 36 pages.
"Notice of Allowance", Australia Patent Application No. 2019240484, Oct. 27, 2021, 4 pages.
"Extended European Search Report", European Patent Application No. 19772545.0, Nov. 16, 2021, 8 pages.
"Office Action", India Patent Application No. 202027033318, Nov. 18, 2021, 6 pages.
"Office Action", Australia Patent Application No. 2018409860, Nov. 30, 2021, 4 pages.
"Office Action", Australia Patent Application No. 2018403182, Dec. 1, 2021, 3 pages.
"Office Action", Korea Patent Application No. 10-2020-7028606, Oct. 29, 2021, 7 pages [14 pages with translation].
"Office Action", Japan Patent Application No. 2020-543924, Nov. 24, 2021, 3 pages [6 pages with translation].
"Extended European Search Report", European Patent Application No. EP19785057, Dec. 6, 2021, 8 pages.
"Office Action", Australia Patent Application No. 2020218172, Dec. 21, 2021, 4 pages.

(56) References Cited

OTHER PUBLICATIONS

"Extended European Search Report", European Patent Application No. 21187314.6, Dec. 10, 2021, 10 pages.

* cited by examiner

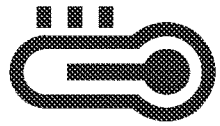
FIG. 12

© addison care

Log out

Are you experiencing any of the following symptoms?

- Sore Throat
- Chills
- Cough
- Headache
- Shortness of Breath
- Repeated Shaking with Chills
- Muscle Aches

FIG. 13

SYSTEMS AND METHODS FOR MITIGATING THE SPREAD OF INFECTIOUS DISEASES

CROSS-REFERENCE TO RELATED APPLICATIONS

The present application claims the priority benefit of U.S. Provisional Patent Application Ser. No. 63/055,236 filed on Jul. 22, 2020 titled "Systems and Methods for Mitigating the Spread of Infectious Diseases," and the present application claims the priority benefit of U.S. Provisional Patent Application Ser. No. 63/067,757 filed on Aug. 19, 2020 titled "Systems and Methods for Reopening Venues and Businesses Through Mitigation of the Spread of Infectious Diseases," which are incorporated by reference in their entireties.

SUMMARY OF EXEMPLARY EMBODIMENTS

According to some exemplary embodiments, a system is provided comprising a hardware processor executing instructions stored on a non-transitory media, the instructions for a method for providing real-time assessment of a potential risk of an infectious disease without face-to-face interaction between a human user and a human healthcare professional, the method including receiving a predetermined acceptable range for an aspect of a human user's physiological measurement data, receiving a predetermined acceptable answer for a survey response question, securely receiving an aspect of the human user's physiological measurement data, determining if the aspect of the human user's physiological measurement data is within the predetermined acceptable range, if the aspect of the human user's physiological measurement data is within the predetermined acceptable range, transmitting to the human user a survey comprising a question, if the aspect of the human user's physiological measurement data is not within the predetermined acceptable range, transmitting an active alert and not providing the human user with the survey comprising a question, and if the human user fails to transmit an acceptable answer to the survey comprising the question, transmitting an active alert.

In further exemplary embodiments, if the aspect of the human user's physiological measurement data is not within the predetermined acceptable range, infectious disease exposure risk survey questions may be transmitted to the human user. Additionally, an active alert may be transmitted to a graphical user interface. A login may be received from the human user and an active alert may be sent if the login from the human user is not received.

Some exemplary systems may be embedded within a kiosk. The survey may be presented with a networked interactive animated conversational graphical user interface configured to provide, in real-time, a consultative recommendation. The human user's physiological measurement data may include temperature, oxygen saturation, weight, blood glucose level, and blood pressure data and may be received from a networked or non-networked peripheral device. The peripheral device may be any of a thermometer, pulse oximeter, blood pressure monitor, spirometer or a scale and may have a hardware processor.

Certain exemplary embodiments may determine and display a potential risk of an infectious disease, including displaying, in real-time, a warning of a potential risk of an infectious disease based on multivariate analyses through supervised and unsupervised machine learning approaches. The displaying may also include securely transmitting the human user's physiological measurement data and survey answer using HIPAA-compliant AES-256 bit encryption. A cloud-based normative data storage having a normative data threshold, a risk ratio, and a recommendation may be accessed and the human user's physiological measurement data may be compared to the normative data threshold and the risk ratio. Based on the comparison, a warning or an approval to enter a facility may be determined and the warning or the approval to enter a facility may be transmitted through the AES-256 bit encryption.

A mobile device, according to various exemplary embodiments, may have an application for the displaying and transmitting of information from and to the system. The information may be used to determine whether access will be granted to an event or venue, and the information may be displayed as a QR code. Additionally, an electronically transferable access pass to an event or venue may be included and the electronically transferable access pass to the event or venue may only be transferable to another device with access granted to the event or venue.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIG. 12 shows an exemplary representative screen image returned when biometric data falls outside of a specified range.

FIG. 13 shows exemplary infectious disease exposure risk survey questions for completion when biometric data falls outside of a specified range.

DETAILED DESCRIPTION

Figure 1:
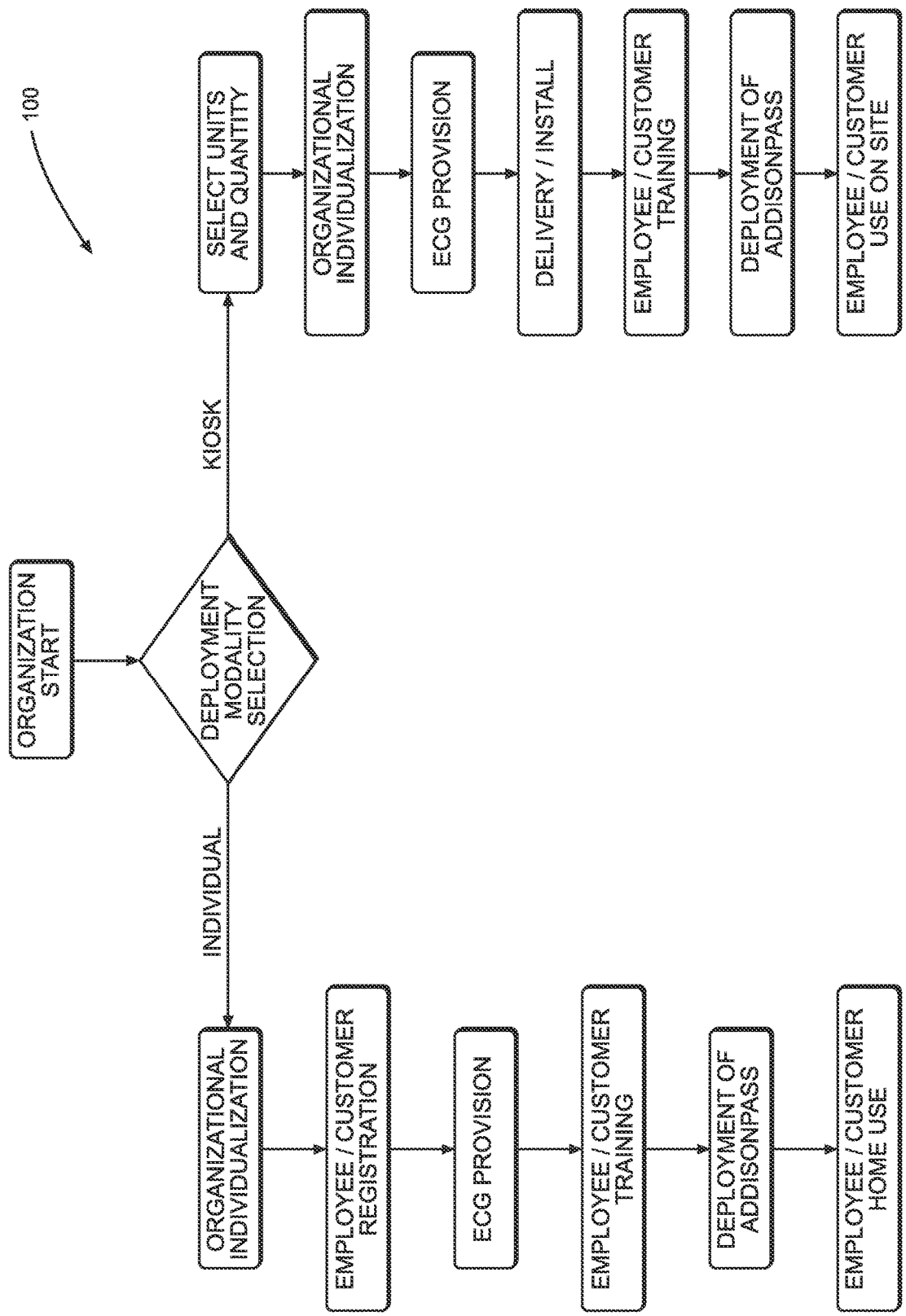
FIG. 1 shows exemplary available delivery modalities and initial process flow.

Part I. AddisonPass™ Platform Overview
Introduction

The Electronic Caregiver (ECG) AddisonPass™ Access Management Program (AddisonPass) is a technology platform allowing the assessment and monitoring of individuals prior to their entry into a specified facility, venue, academic institution or business. Integration of AddisonPass™ allows individuals to efficiently enter these areas by analyzing the answers to questionnaire(s) from health organizations (e.g., CDC, WHO) and verified biometric data through a secure, password protected web and/or mobile application providing a pass/fail result for entry. Organizations (e.g., schools, businesses, Houses of Worship) are thus better able to identify and proactively manage entry without having to apply separate resources, manually track symptomology, or manage access at point-of-entry at significant additional costs and logistical complexity. The AddisonPass™ platform specifically allows individuals to proactively and confidentially track symptomology and make better informed choices regarding health status and whether or not to proceed to a venue. Moreover, the questions around symptomology can be adjusted in real-time based on health organization recommendations as well as responses provided to prior questions, thus creating a dynamic assessment of health and wellness of the individual. AddisonPass™ also supports organizations in maintaining individual and customer safety, as well as reducing the amount of time employees lose to illness by reducing the likelihood of spread. Importantly, this system can be integrated into schools, universities, and additional 'superspreader' environments where many people gather. With this data, organizations can confidently inform employees and customers whether to work, study, and shop remotely, or to proceed to the venue for an in-person experience. Adoption of the AddisonPass™ platform on an individual, business and community level allows for a single, consistent and reliable system to manage entry across multiple organizations without inconsistency in collection and reporting methodology, and at significantly lower cost and risk as compared with other current models. Additionally, capture of this data can be combined with publicly available test results to improve the science behind understanding prevalence of symptomology, length of symptomology and other infectious disease information for the betterment of public health efforts around any pathogen. Importantly, this model can improve efficiency in operations while minimizing manual efforts and the number of staff needed to manage the reentry process as safely as possible.

Acronyms

AES—Advanced Encryption Standard
AWS—Amazon Web Services
ECG—Electronic Caregiver, Inc
GCP—Google Cloud Platform
GUI—Graphical User Interface
HIPAA—Health Insurance Portability and Accountability
IUM—Individual Use Model Part 2. AddisonPass™ Product Types
Introduction The typical end-user will enroll in the ECG AddisonPass™ platform. This will allow the individual to perform screening via biometric data and questionnaire survey inputs on a web-connected device to create a pass/fail result specific to the infectious disease being monitored. A pass result indicates that the individual may be allowed into the venue based on their questionnaire and biometric data, while a fail result indicates that they should not be allowed entry. The pass/fail result can be stored on their phone as a unique scannable code to be presented as a verified, digital, trusted certificate of safety at point-of-entry to a venue. Though the specific answers to screening questions will be available to the end user, the only information accessible to organizations (captured via mobile device, tablet, or other internet-connected or Bluetooth® device), besides demographics data associated with the individual, will be the pass/fail result. End-user protected health information will not be available to organizations. In some embodiments, a credentialed organization member may log into a dashboard to view the data. Participating organizations would then use either a kiosk model or a manual checking process to scan this code and track approved entry versus unapproved entry. This is similar in principle to a TSA agent checking for "TSA Pre-Check" on a passenger's ticket. The process for scanning mobile phones for tickets is widely used now at airports, concert halls, and sporting arenas, and therefore this physical infrastructure could be leveraged at nominal expense for this additional screening. This is expected to be significantly more efficient and comprehensive than a superficial manual screening at point-of-entry for attendees. The ECG platform will be supported on multiple platforms and through available scanning devices, as this decision is the purview of the organization. By providing various options related to platform deployment, ECG can enhance market penetration opportunities and provide customer-centric, iterative versions of the AddisonPass™. The current delivery modalities available for the ECG AddisonPass™ include an individual use model and a kiosk deployment model, as represented in FIG. 1.

FIG. 1 shows available delivery modalities for ECG AddisonPass™ and initial process flow 100.

2.1 Individual Use Model

The individual use model for deployment provides disparate organizations, through a web application that can monitor activity on an individual level, with actionable data describing infectious disease exposure risks. Based on the ability for an individual to report symptomology and biometric data, the pass/fail score can be read at entry points for a given individual. The pass/fail result is determined using both machine learning and prescribed acceptable ranges of responses to determine an individual's relative risk of infection. After an organization completes the onboarding process, ECG is responsible for provisioning their individual-specific login credentials and providing those login credentials to the organization.

2.2 Organizational Use Model

Organizations, who may incorporate this system as part of a program for a wide variety of purposes for its customers (e.g., rewards or incentive program, financial insurance program, safety initiative), may also provide this program on behalf of their customers. For instance, users could be identified by the organization and ECG would provide log in credentials to the identified users. In this case, the organization is responsible for payment of fees (whole or partial) depending on their reward and incentive rules. Regardless of the exact usage scenario, the delivered results to the end user would be scanned at a kiosk or through other scanning methodology at point of entry at participating organizations.

Figure 2:
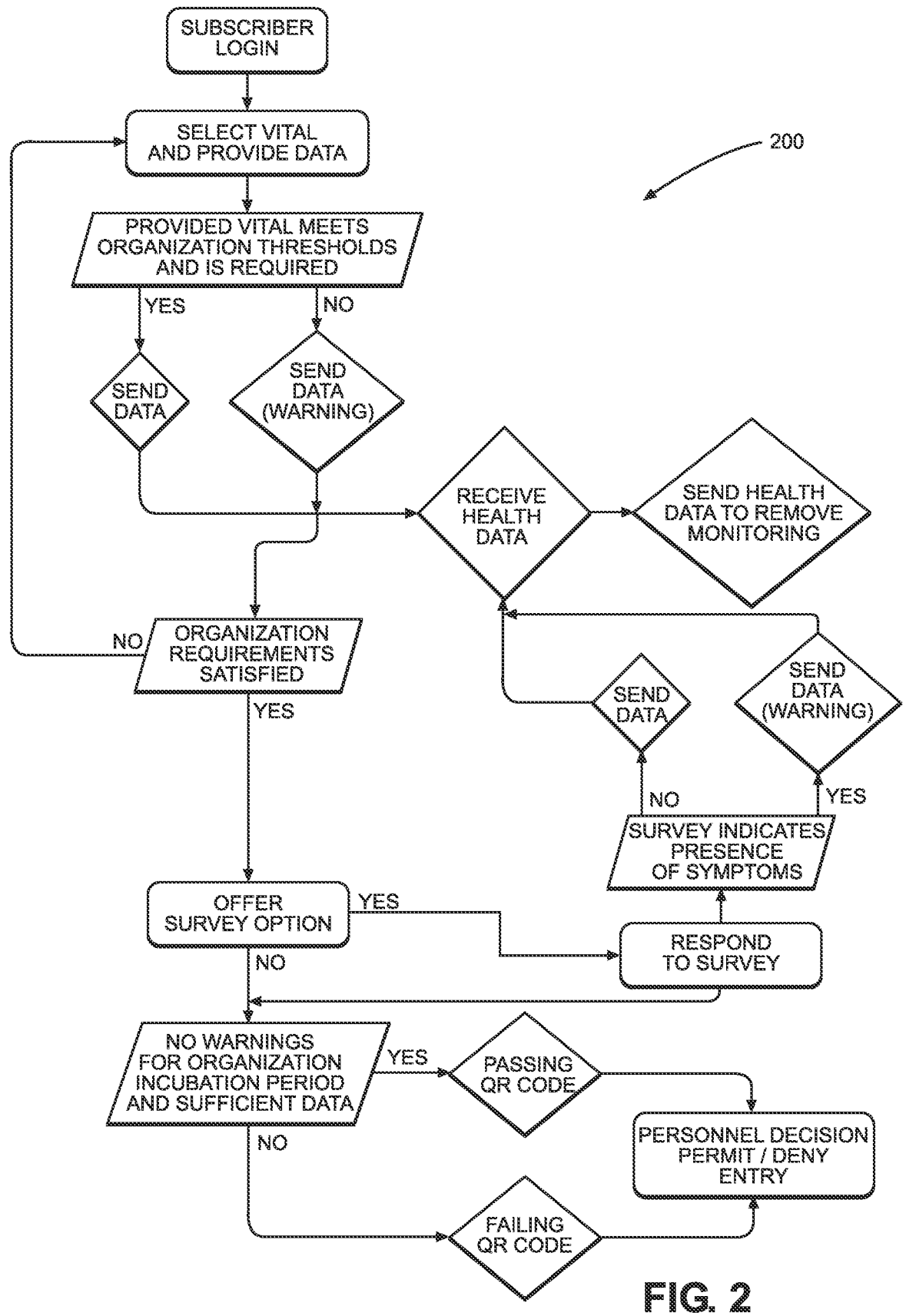
FIG. 2 shows an exemplary imbedded intelligence and active alert flowchart.

FIG. 2 shows an imbedded intelligence and active alert flowchart 200.

Data collected via the AddisonPass™ platform may also be routed to an interactive GUI and notification system for review by an individual (or a team of individuals) designated to make decisions concerning entry to a facility. Additionally, machine learning algorithms imbedded within the platform, as depicted in FIG. 2, makes available the capacity to provide alerts to the organization's team monitoring employees/customers through the Graphical User Interface (GUI). Through these processes and procedures, the AddisonPass™ Access Management platform provides organizations with the capacity to assess exposure risk associated with infectious disease transmission prior to having employees/customers enter the facility, ultimately reducing the risk associated with possible exposure.

Figure 3:
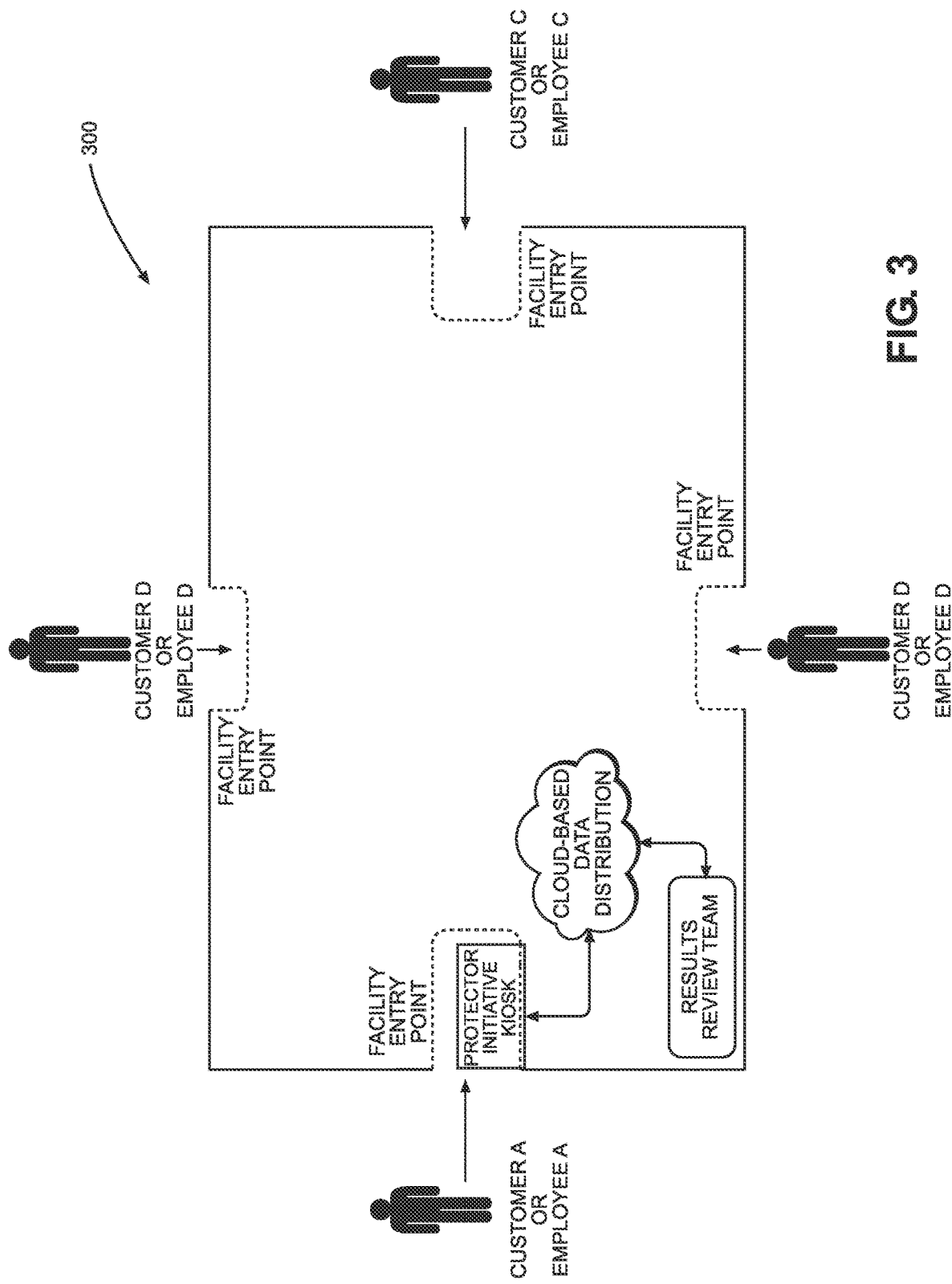
FIG. 3 shows an exemplary demonstrated access point control schematic for facility entry control using the kiosk deployment model.

FIG. 3 shows a demonstrated access point control schematic 300 for facility entry control using the kiosk deployment model.

As depicted in FIG. 3, the AddisonPass™ kiosk (see FIG. 4) or other scanning device is positioned at the point of Employee/Customer entry. Prior to entering the facility, Customer/Employee A scans the pass/fail code from their mobile device. As with the individual use model, machine intelligence imbedded within the kiosk model provides the capacity to deliver alerts to the organization's team monitoring user data through the GUI as displayed in FIGS. 16 and 17. Following review of the data by the organization monitoring team, a determination can be made to allow/deny entry based on defined organizational standards. Additionally, as can be inferred from FIG. 3, the deploying organization has the option to determine level of facility access control by providing an AddisonPass™ kiosk at single point of entry as displayed in FIG. 3, or at any combination of multiple entry points.

Figure 4:
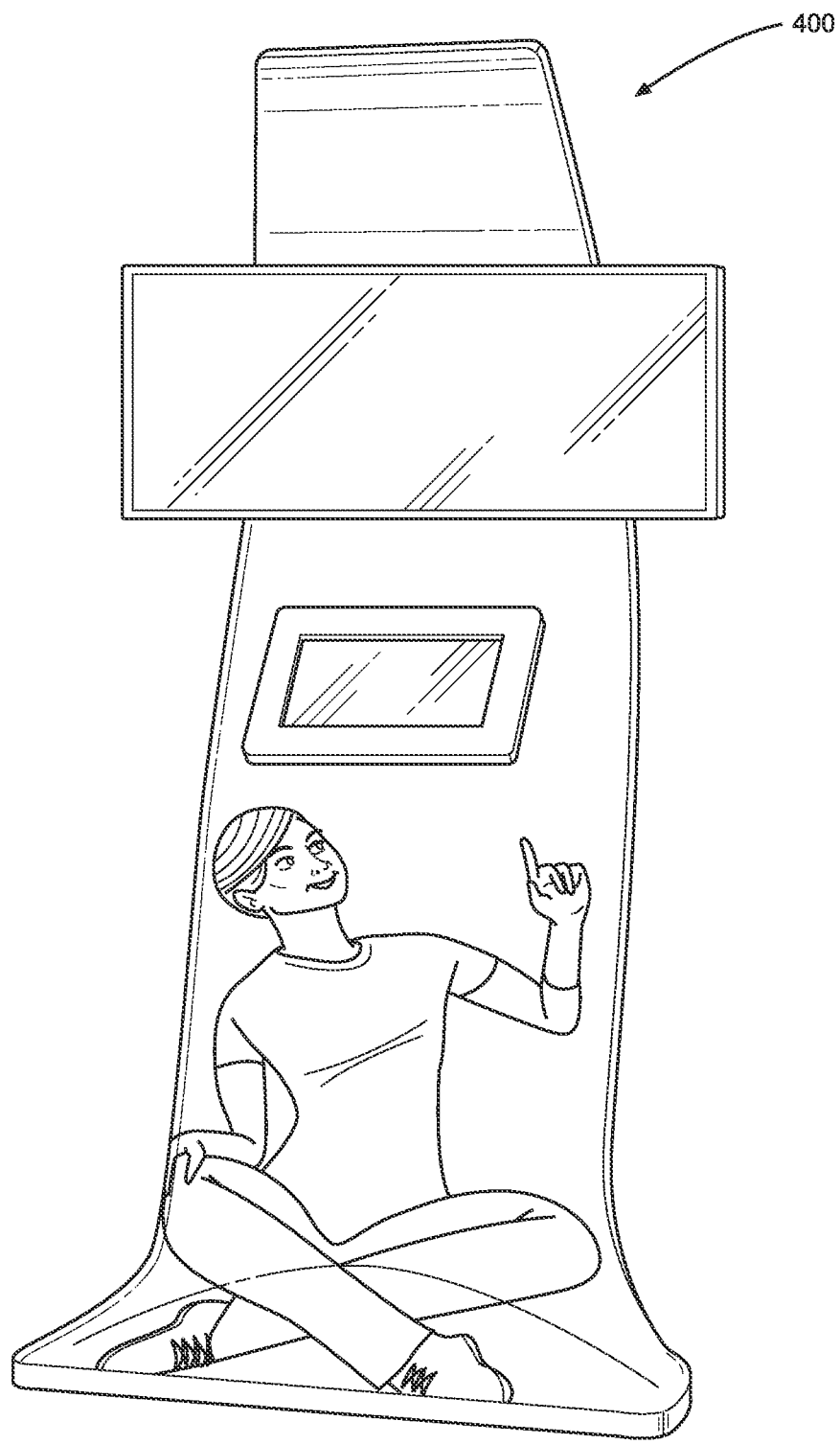
FIG. 4 shows an exemplary style of an AddisonPass™ kiosk.

FIG. 4 shows an example style of an AddisonPass™ kiosk 400.

Figure 5:
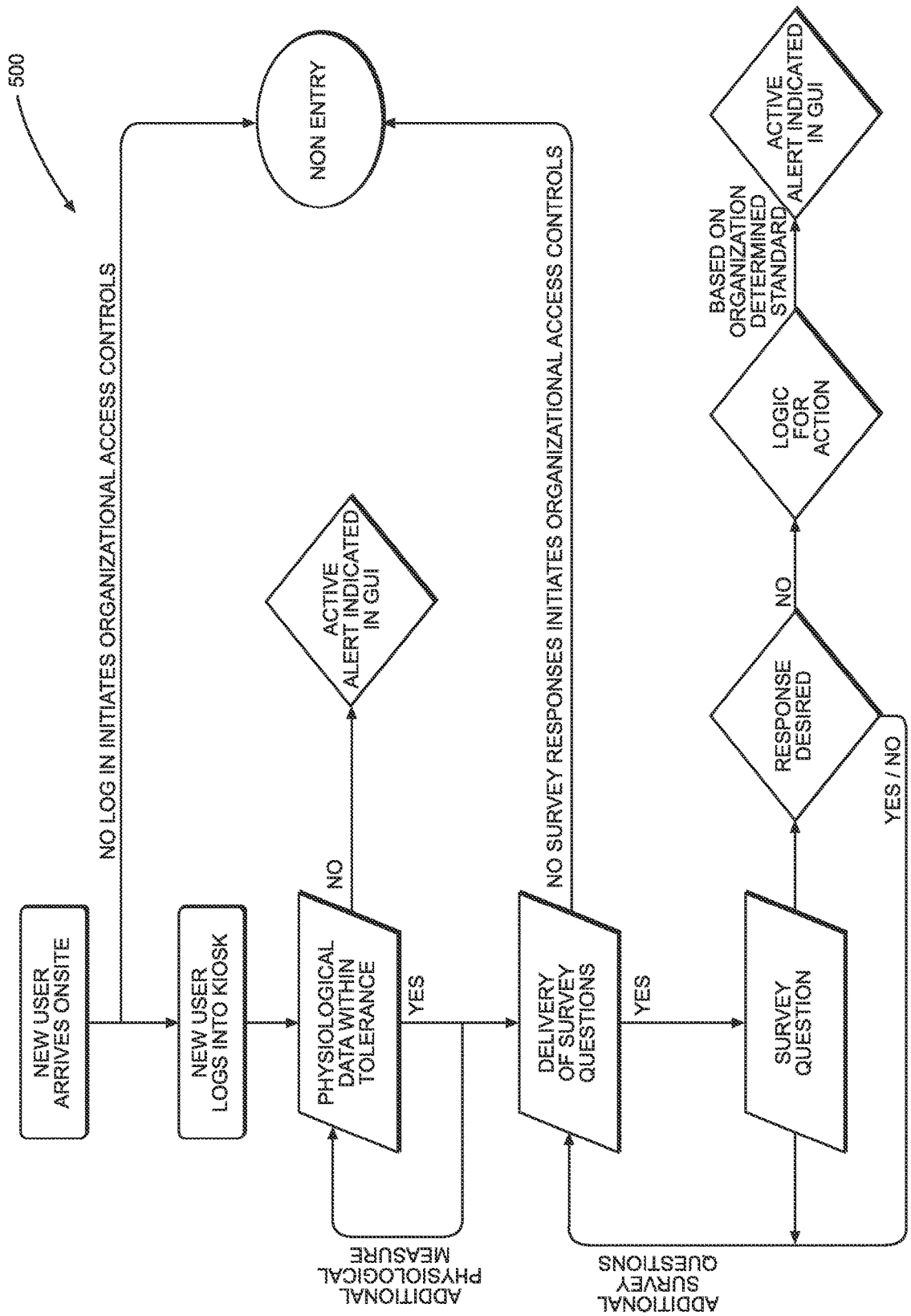
FIG. 5 shows exemplary kiosk model logic for creation of an active alert for organizational review.

FIG. 5 shows kiosk model logic 500 for creation of an active alert for an organization to review.

2.3 Insurance Product in Individual Risk Protection Model

The AddisonPass™ Access Control Management platform can also be used in conjunction with a form of individual protection at the event, business or venue level (e.g., concerts, sporting events). In one case, the individual participates in a 'pool,' such that if they are unable to participate or attend an event, they can sell or trade their 'ticket' with someone in the pool who is not potentially ill. This creates incentive for any individual user to answer honestly as it minimizes risk of potential financial damages. Support to venues and events is provided by minimizing risks of potentially ill attendees going to events, while maximizing chances of filling venues to capacity.

The AddisonPass™ Access Control Management platform could also be used as part of an insurance program that allows sharing of risk across populations. Similar to other types of trip or travel interruption insurance, or insurance made available for ticket purchases through a broker such as TicketMaster, this model supports honest self-reporting of symptomology by individuals and minimizes financial risk. Importantly because this model provides some protection from financial risk to the individuals as noted above, it minimizes the risk of spread of infection within the community while allowing maximum access to services and products that are a vital part of the economy. This form of rewarding desired behavior and minimizing negative consequences for self-reporting is important not only for the economy, but also for helping to create a culture of acceptance and fostering a positive vision of a post-pandemic society.

Part 3. AddisonPass™ Work/Data Flows
Introduction

Data flows are designed to provide real-time, actionable data to organizations/clinicians. This platform effectively functions to reduce the risk of disease spread, improve workplace safety and provide high-confidence access to the safety of venues.

3.1 Health Insurance Portability and Data Privacy (e.g., HIPAA and GDRP) Compliance Individual privacy and data security are two factors that have been integrated into the AddisonPass™ platform from product inception through product delivery. All data collection and transmission occurring via the ECG AddisonPass™ platform are compliant with HIPAA requirements. All data are AES-256 bit encrypted upon ingestion into the end-user hardware and remain encrypted through transit and deposit into the ECG cloud-hybrid infrastructure. All data remain AES-256 bit encrypted at rest within the system as well.

3.2 Organizational Workflow

The workflow presented herein is deployable across a wide spectrum of infectious diseases. In general, upon registration of an organization (i.e.—school, employer, business, House of Worship, etc.) for AddisonPass™ use, ECG will immediately work to establish an account for the organization. Once ECG has registered the organization, ECG will provide them with all affiliated users login information. Upon receipt of login information, the organization provides credentials to their registered users.

Once a registered user has received their login credentials, the user will log into the platform and follow the provided prompts. This workflow is depicted in FIG. 6.

Figure 6:
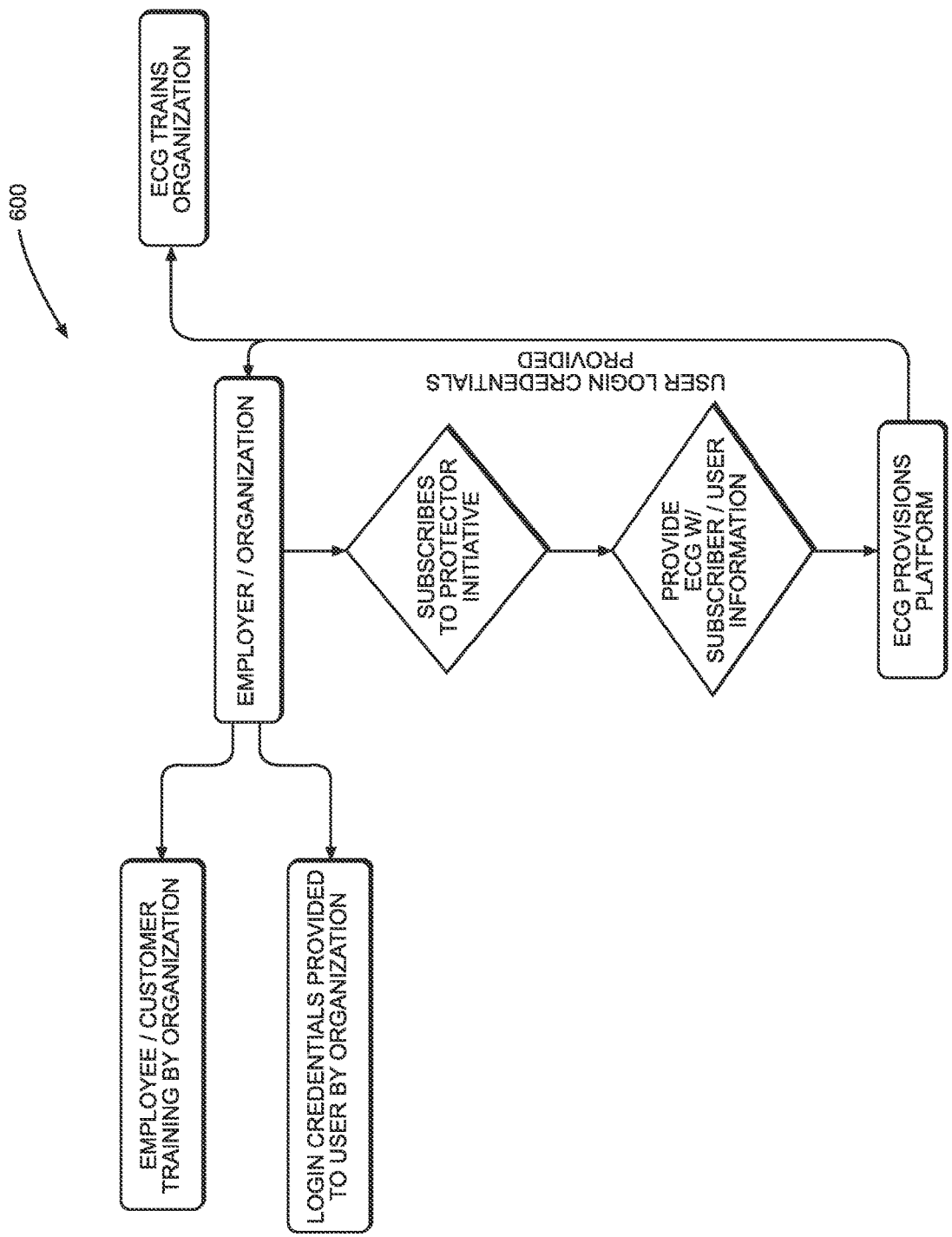
FIG. 6 shows exemplary workflow surrounding AddisonPass™ organization onboarding, training and delivery process.

FIG. 6 shows workflow 600 surrounding ECG AddisonPass™ employer/organization onboarding, training and delivery process.

Following the completion of the onboarding, training and delivery processes associated with AddisonPass™, the platform is now available for implementation and use. To use the platform, an end user (e.g., employee, customer) will log into the AddisonPass™ portal and complete the infectious disease risk assessment as depicted in FIG. 7.

Figure 7:
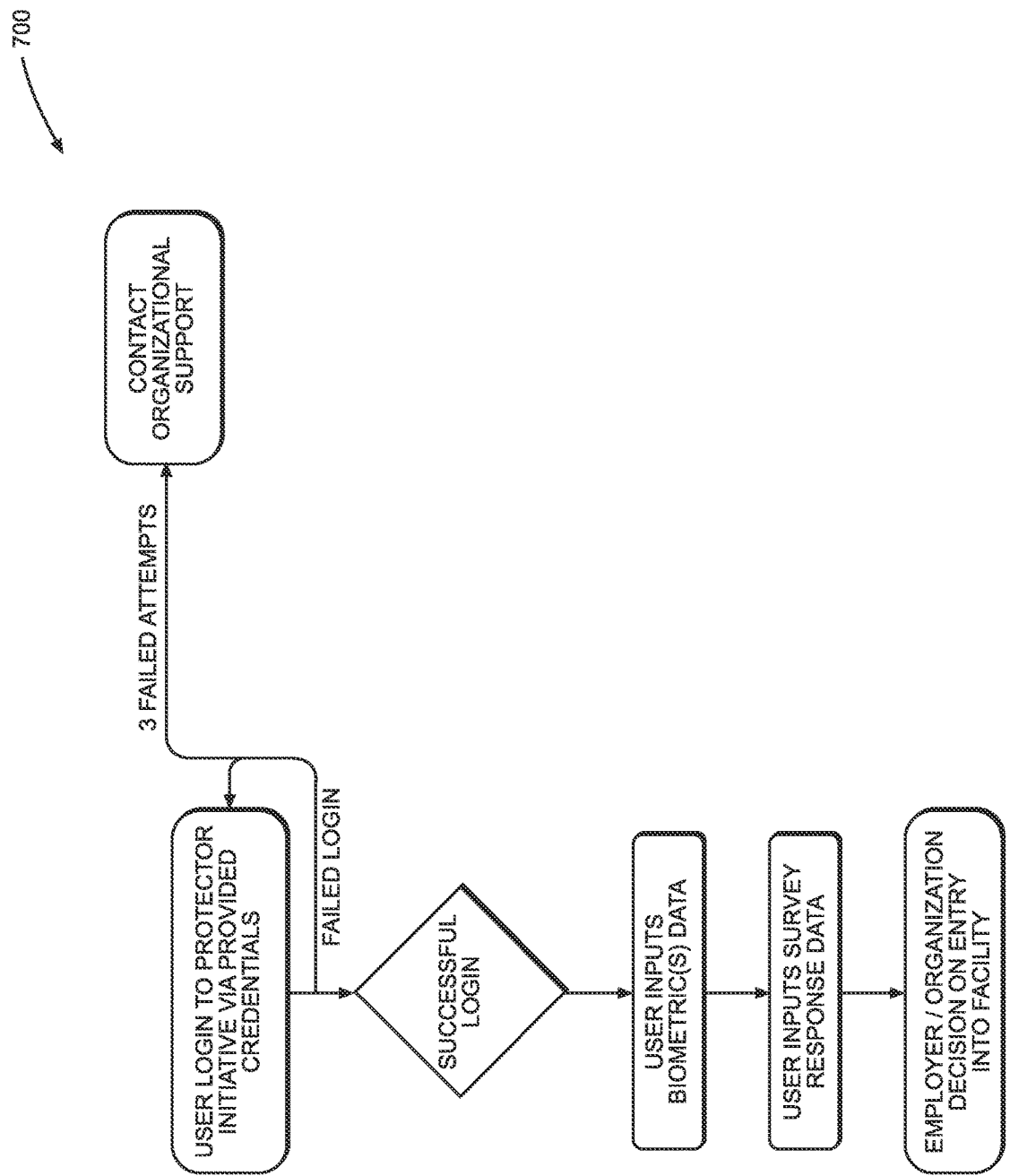
FIG. 7 shows exemplary workflow for end user completion of infectious disease risk assessment.

FIG. 7 shows a workflow 700 for end user completion of infectious disease risk assessment.

3.3 AddisonPass™ Data Flow

Figure 8:
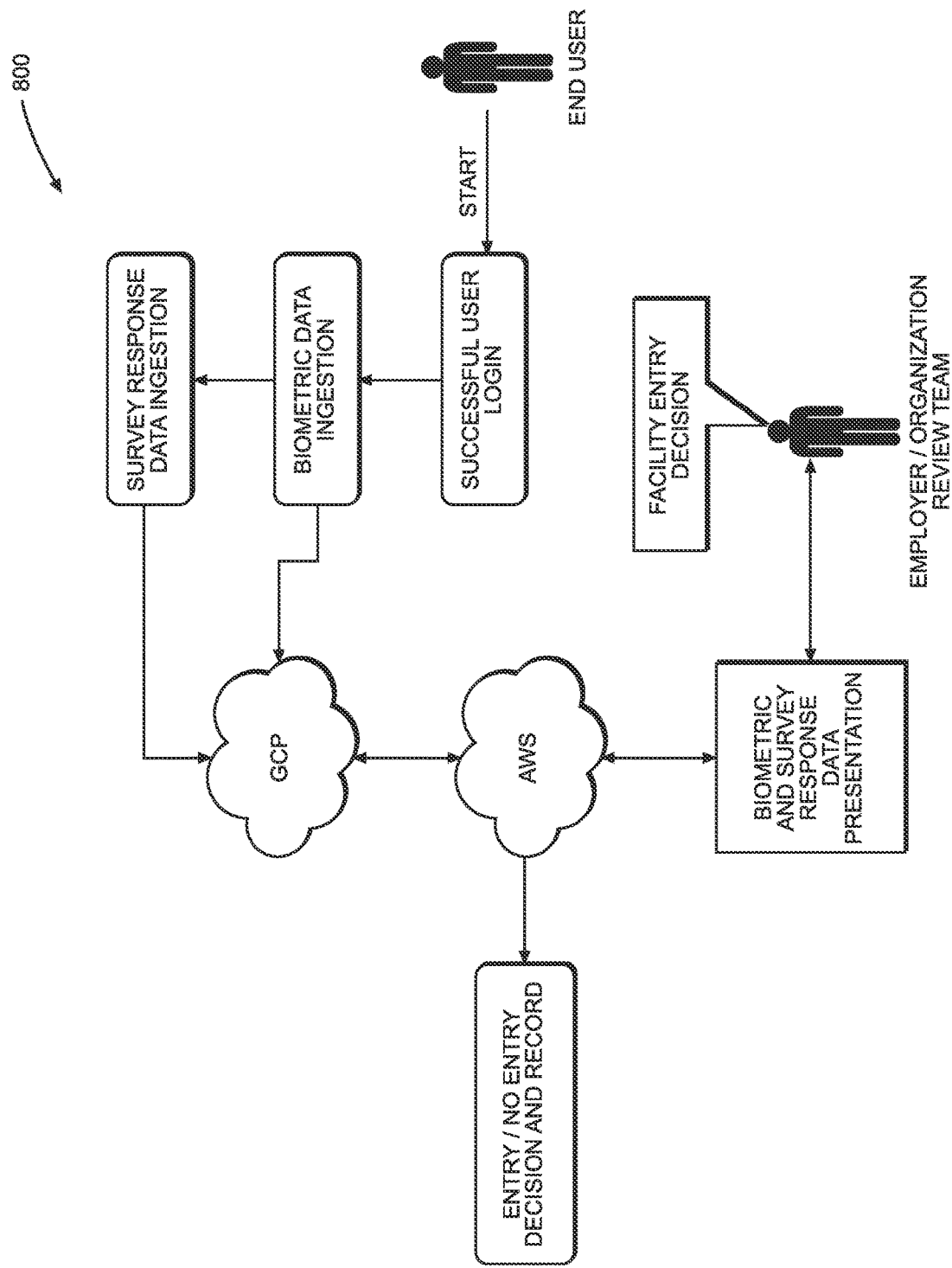
FIG. 8 shows an exemplary AddisonPass™ infectious disease mitigation platform data flow.

FIG. 8 shows ECG AddisonPass™ infectious disease mitigation platform data flow 800. As displayed in FIG. 8, all data are ingested into the private and secure Google Cloud Platform (GCP)/Amazon Web Services (AWS) platform. All user login, biometric and survey data are end-to-end encrypted using AES-256 bit encryption. This encryption includes periods of both data transmission (in-transit) and data storage (at rest).

Part 4. AddisonPass™ User Interfaces
Introduction

Collecting data describing biometric data and survey responses as they relate to risk of infectious disease spread is one functional aspect of the AddisonPass™. The second functional aspect of the platform is to provide an interface through which the platform delivers these data to a remotely accessible portal for review by the contracting organization. This portal provides decision makers within the organization with access to user survey response and biometric data without in-person, physical contact—which is critical during times of infectious disease spread and risk. This protocol design allows organizations to safely screen users and proactively address risk of exposure to infectious disease based on their defined levels of risk tolerance. By providing a method for front-end user experience through the AddisonPass™ web application and delivering a backend user experience through the AddisonPass™ Dashboard, ECG can collect and deliver biometric and survey response data via user friendly interfaces in a HIPAA compliant manner.

Through enhanced engagement, employers/organizations are provided with the capacity for making real-time, case-by-case determinations of whether a front-end user should enter a facility. This allows employers and organizations to maintain their independence and autonomy in safely managing access to their facilities. In doing so, employers and organizations can limit the unintended spread of infectious disease by asymptomatic carriers. Successfully adopting the ECG AddisonPass™ platform enables organizations to re-open to employees and customers in an informed, data-driven manner. Additionally, by demonstrating evidence of data-driven decisions, employers/organizations can better provide employees/customers with higher levels of confidence and peace-of-mind when entering new environments. Together, this will significantly reduce unintended disease spread while simultaneously enabling a reopening of economic activity.

4.1 AddisonPass™ Front End User Experience

The ECG AddisonPass™ provides an interactive front-end user experience. When provided with login credentials by their employer/organization, the front-end user is also provided with a link to the application portal. By selecting the link, the front-end user is directed to the appropriate web portal site. Upon reaching the designated site, the front-end user is presented with the login screen displayed in FIG. 9.

Figure 9:
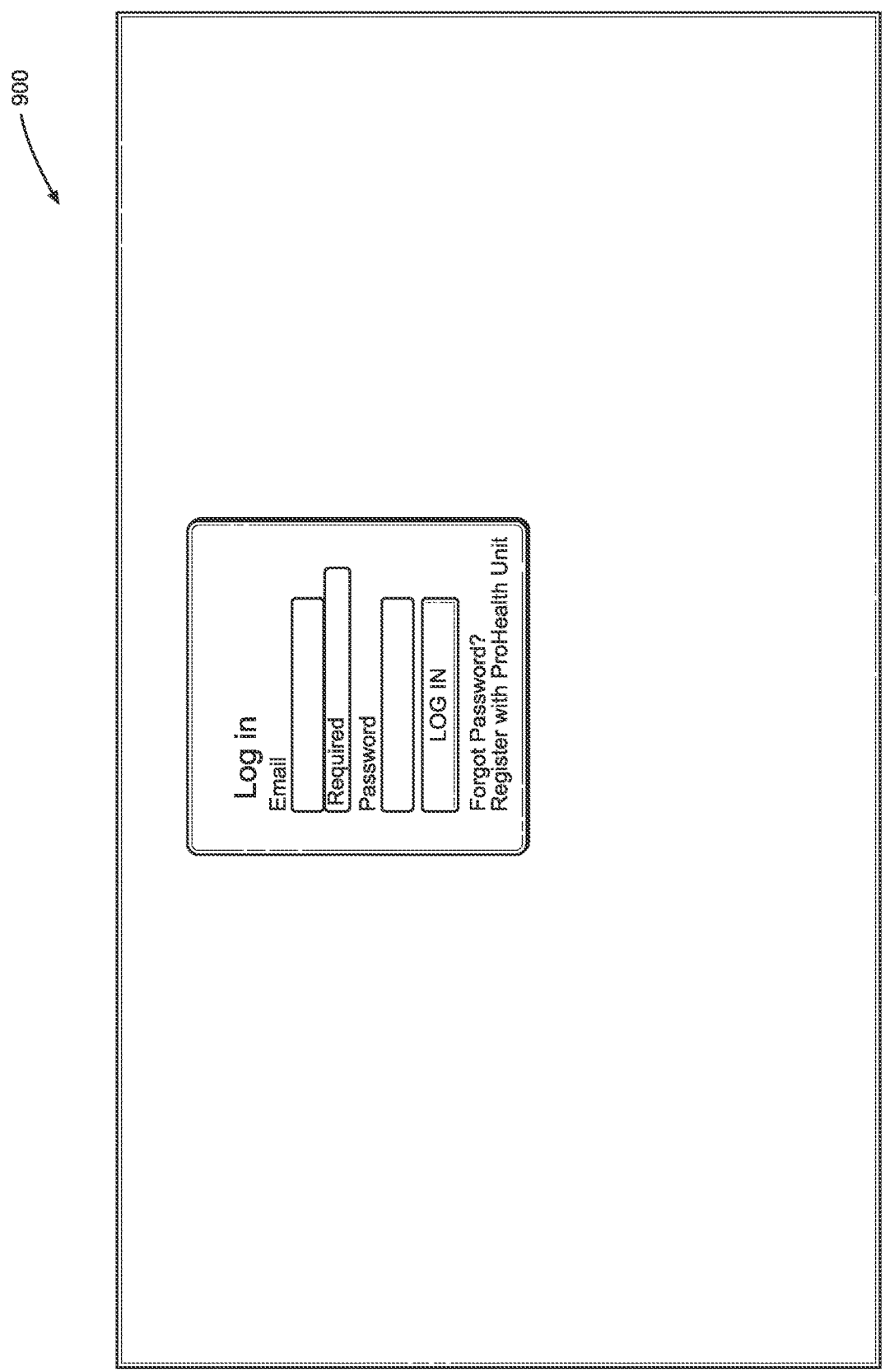
FIG. 9 shows an exemplary login screen for AddisonPass™ infectious disease mitigation platform.

FIG. 9 shows a login screen 900 for the ECG AddisonPass™ infectious disease mitigation platform.

Figure 10:
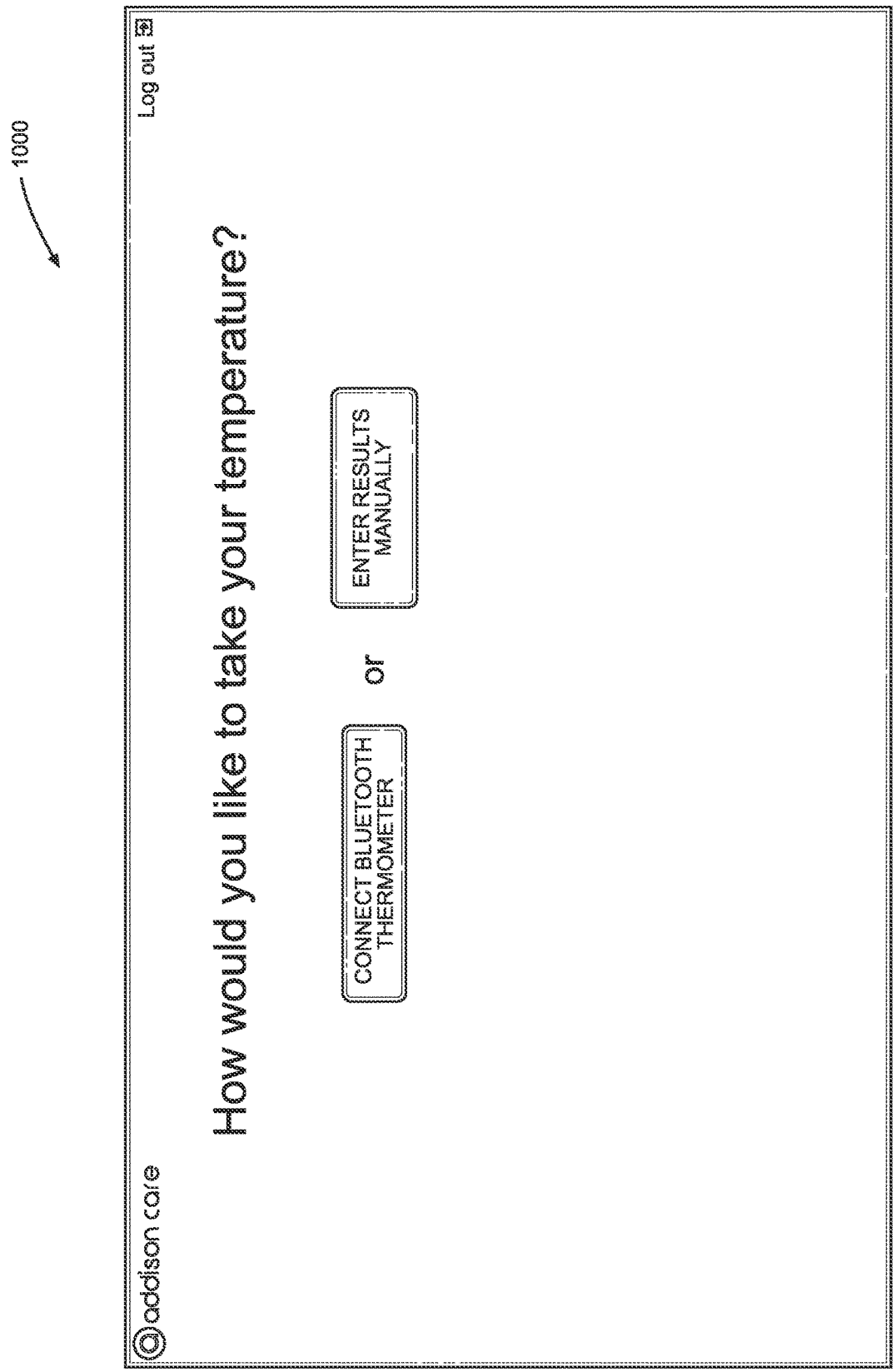
FIG. 10 shows an exemplary data entry mode selection screen following initial login.

Once logged in, the front-end user is directed to a page requesting a selection for biometric data collection modality as displayed in FIG. 10. Once the front-end user selects the desired data entry mode, they input the indicated biometric data. In instances where the input biometric data falls within an organization's provided range, the front-end user has completed the required steps for entry into the facility and is provided the response displayed in FIG. 11. In instances where the front-end user ingests biometric data not falling within the organization specified range, the ingested biometric data are logged, and the front-end user is presented with the screen displayed in FIG. 12 and then provided the opportunity to re-ingest their biometric data and complete an infectious disease risk assessment.

Following reingestion of biometric data, the front-end user is then provided the survey displayed in FIG. 13 for completion. Once all data have been collected (biometric and survey) all data are displayed in a back-end GUI accessible by organization/employer staff for review as displayed in FIGS. 16 and 17.

FIG. 10 shows data entry mode selection screen 1000 following initial login.

Figure 11:
FIG. 11 shows exemplary results returned if ingested data falls within a specified range.

FIG. 11 shows results returned 1100 if ingested data falls within a specified range.

FIG. 12 shows a representative screen image returned 1200 when biometric data falls outside of a specified range.

FIG. 13 shows infectious disease exposure risk survey questions 1300 for completion when biometric data falls outside of a specified range.

Figure 14:
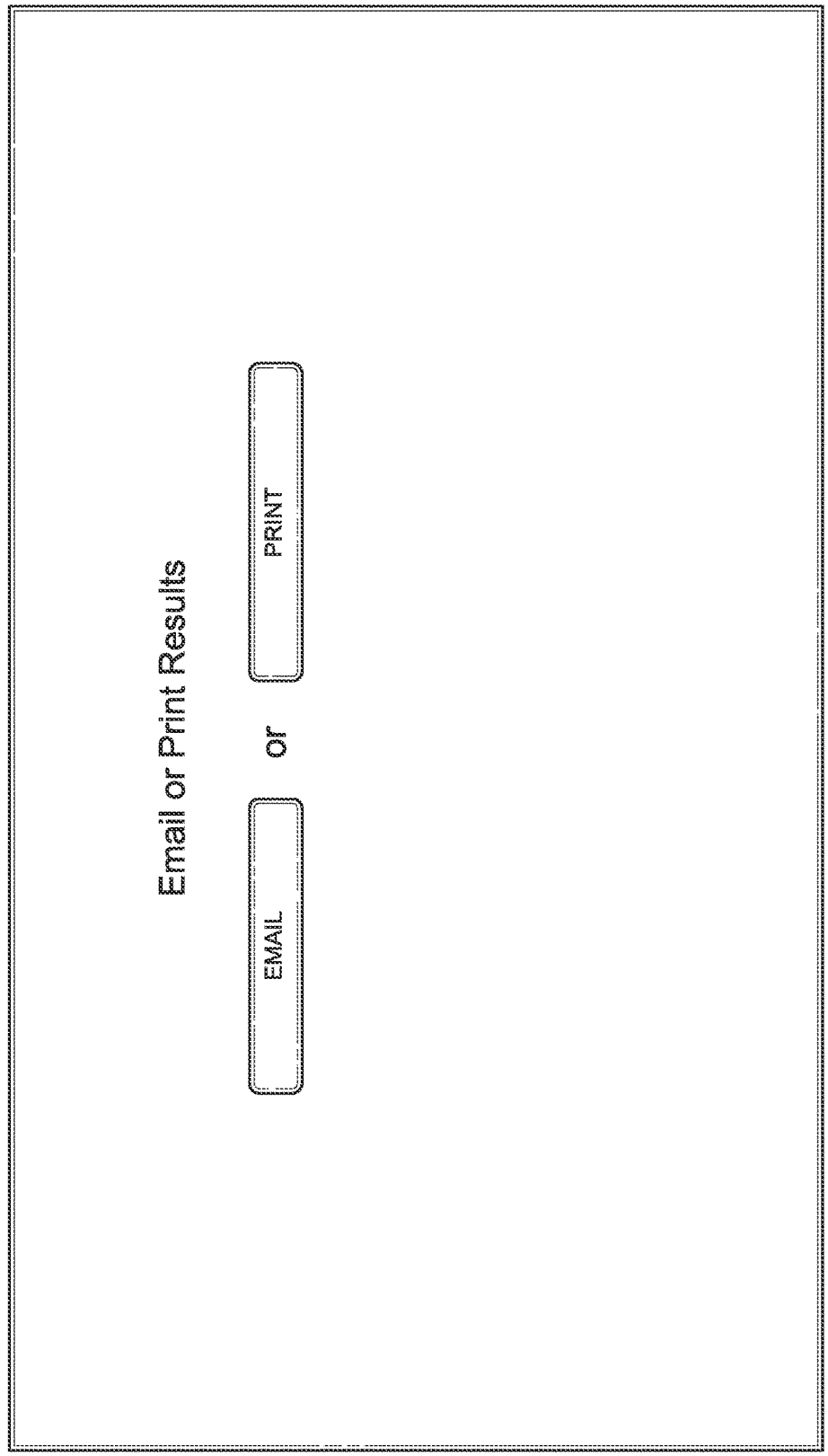
FIG. 14 shows an exemplary screen for allowing a print/email option for AddisonPass™ results.

FIG. 14 shows a presented screen 1400 allowing print/email option for
AddisonPass™ results.

Once all data collection has been completed, the AddisonPass™ front-end user is then presented with the screen displayed in FIG. 14 and presented with the opportunity to email their results to themselves or print their results from a connected printing device.

Figure 15:
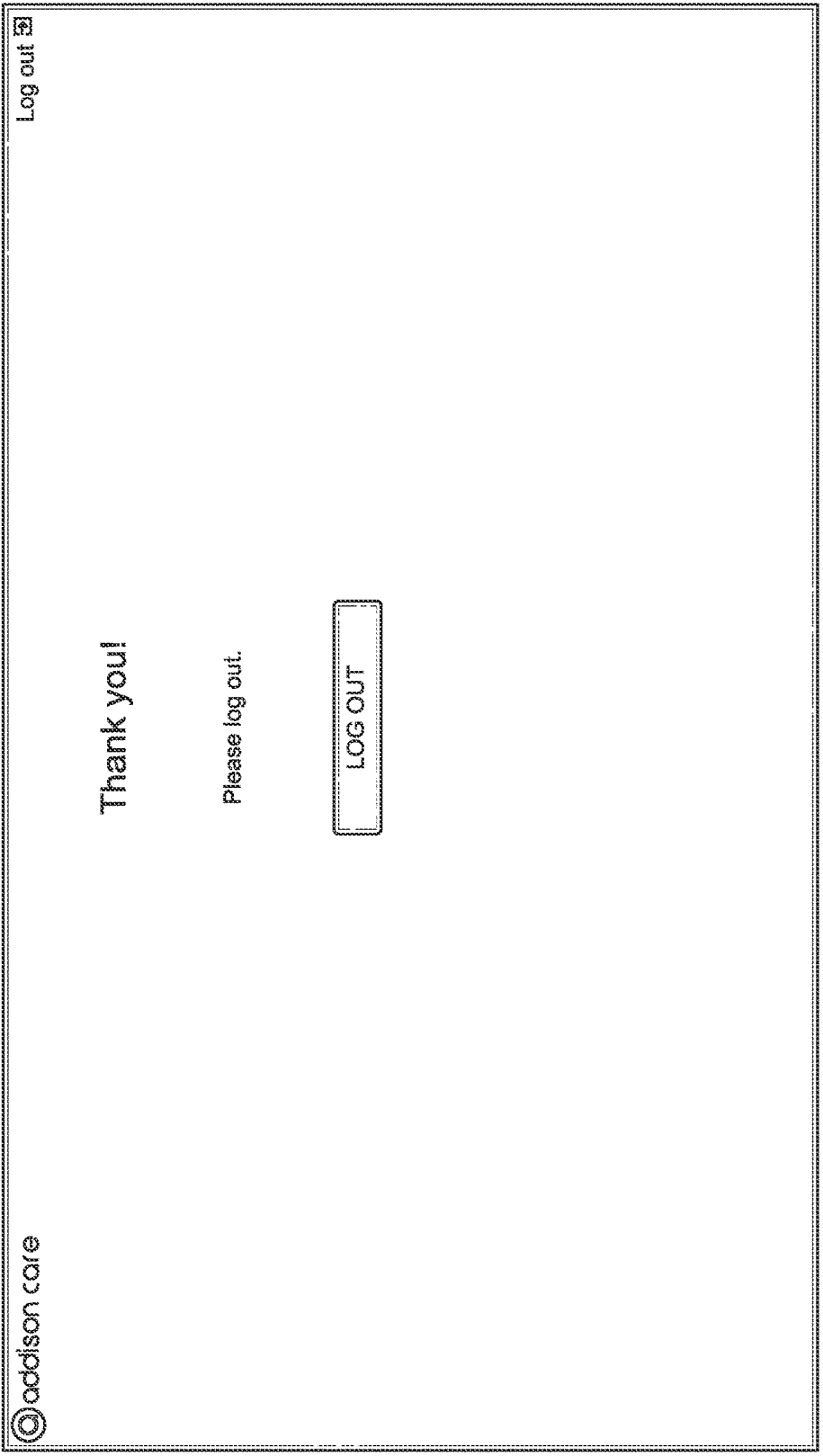
FIG. 15 shows an exemplary log out screen presented to front-end users.

FIG. 15 shows an exemplary log out screen 1500 presented to front-end users.

Back-End User Experience

Figure 16:
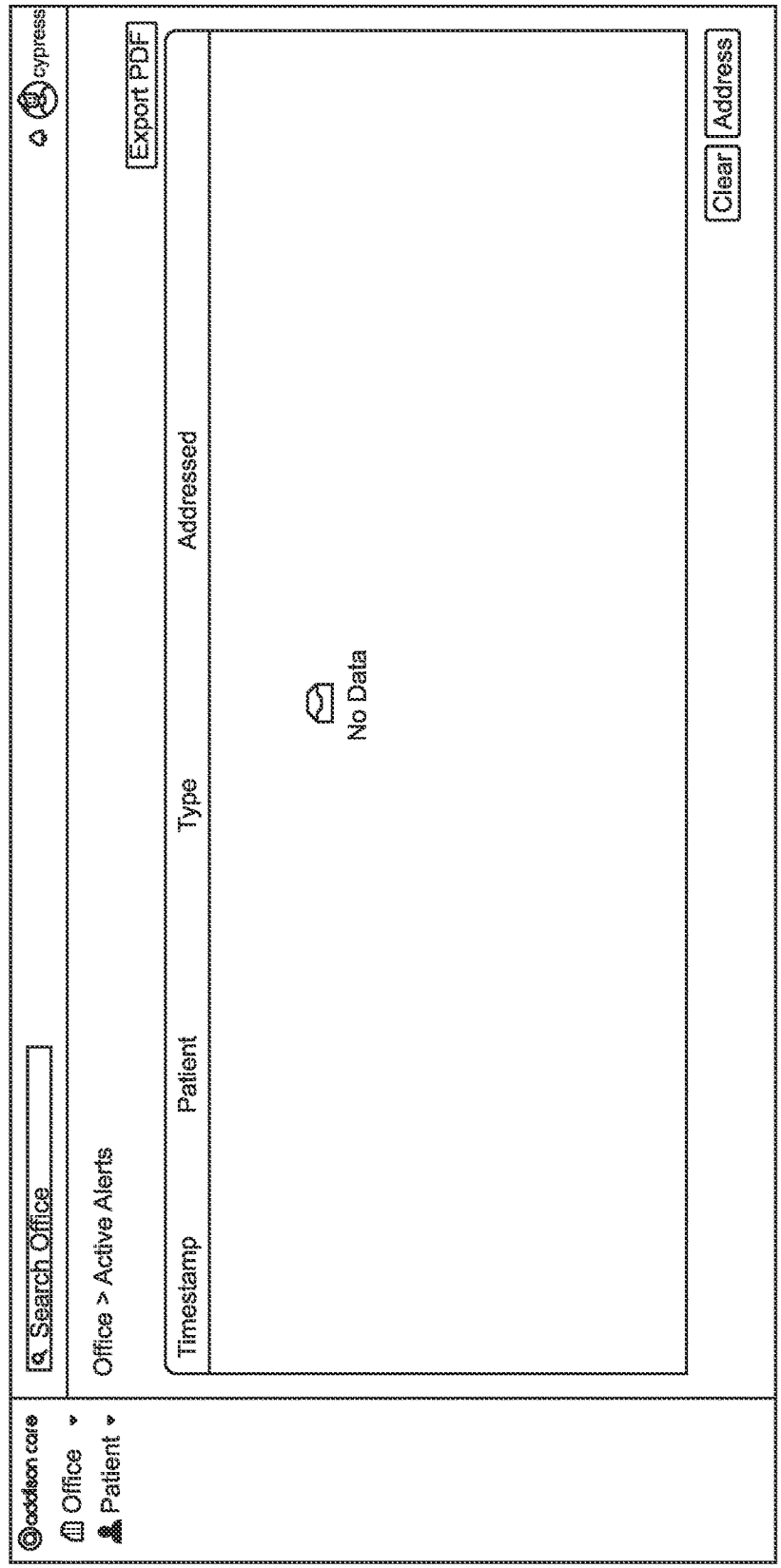
FIG. 16 shows an exemplary dashboard landing screen.

FIG. 16 shows the dashboard landing page 1600.

Figure 17:
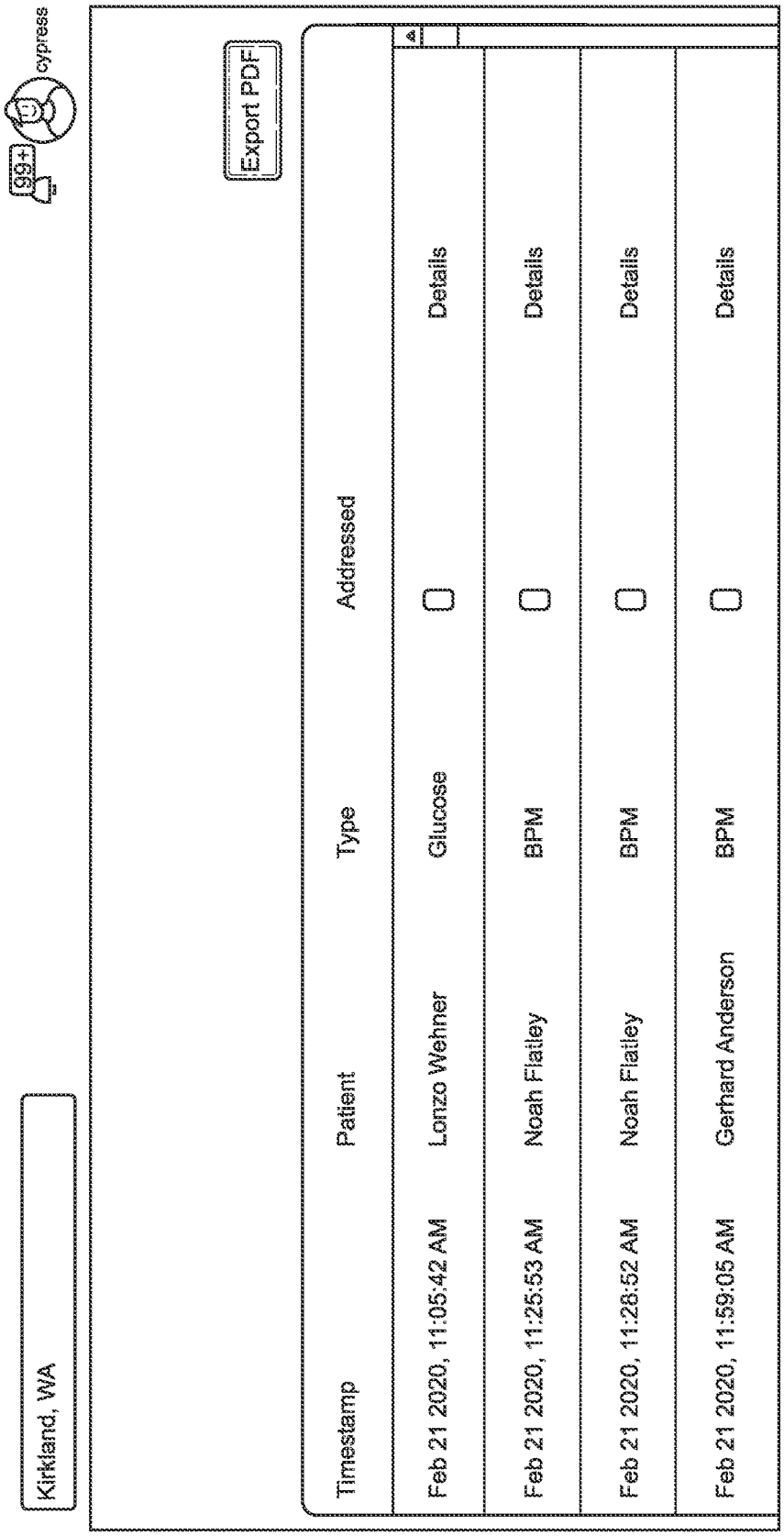
FIG. 17 shows an exemplary AddisonPass™ clinical dashboard displaying a series of active alerts.

FIG. 17 shows an ECG AddisonPass™ clinical dashboard 1700 displaying a series of active alerts.

Following front-end user completion of the AddisonPass™ processes, all data are routed to a data portal which provides an opportunity for back-end users (typically organization designated) to review the data. The AddisonPass™ data portal is a proprietary GUI providing organizations/employers with the capacity for real time delivery of user data, alerts based on system intelligence and the capacity to actively respond to data-centric alerts to mitigate possible exposure to infectious disease. For dashboard use, credentialed organization members log into the data portal with provided credentials to reach the landing page displayed in FIG. 16 and navigate to observe all current active alerts across users for which the organization has yet to respond to data outside or in opposition to the desired response as shown in FIG. 17.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. Exemplary embodiments were chosen and described in order to best explain the principles of the present disclosure and its practical application, and to enable others of ordinary skill in the art to understand the present disclosure for various embodiments with various modifications as are suited to the particular use contemplated.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present disclosure. As such, some of the components may have been distorted from their actual scale for pictorial clarity.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:
1. A system comprising:
a hardware processor communicatively coupled to a mobile device having an application for displaying and transmitting information from and to the hardware processor, the hardware processor executing instructions stored on a non-transitory media, the instructions for a method for providing real-time assessment of a potential risk of an infectious disease without face-to-face interaction between a human user and a human healthcare professional, the method comprising:

receiving a predetermined acceptable range for an aspect of a human user's physiological measurement data;
receiving a predetermined acceptable answer for a survey question;
securely receiving an aspect of the human user's physiological measurement data;
determining if the aspect of the human user's physiological measurement data is within the predetermined acceptable range;
if the aspect of the human user's physiological measurement data is within the predetermined acceptable range, transmitting to the human user a survey comprising a question;
if the aspect of the human user's physiological measurement data is not within the predetermined acceptable range, transmitting an active alert comprising a warning of a potential risk of an infectious disease based on multivariate analyses;
if the human user fails to transmit an acceptable answer to the survey comprising the question, transmitting the active alert; and
presenting a display by the application on the mobile device in response to the human user's physiological measurement data being within the predetermined acceptable range and receiving the predetermined acceptable answer to the survey question from the human user, the display comprising a unique scannable code functioning as an electronically transferable access pass to an event or venue, the electronically transferable access pass being limited in transferability to other human users who have provided physiological measurement data within the predetermined acceptable range and who have further provided the predetermined acceptable answer to the survey question.

2. The system of claim 1, further comprising if the aspect of the human user's physiological measurement data is not within the predetermined acceptable range, transmitting infectious disease exposure risk survey questions to the human user.

3. The system of claim 1, further comprising the active alert being transmitted to a graphical user interface.

4. The system of claim 1, further comprising receiving a login from the human user.

5. The system of claim 4, further comprising sending the active alert if the login from the human user is not received.

6. The system of claim 1, further comprising the hardware processor being embedded within a kiosk.

7. The system of claim 6, further comprising presenting the survey with a networked interactive animated conversational graphical user interface.

8. The system of claim 7, further comprising the networked interactive animated conversation graphical user interface configured to provide, in real-time, a consultative recommendation.

9. The system of claim 1, the human user's physiological measurement data further comprising temperature, oxygen saturation, weight, blood glucose level, and blood pressure data.

10. The system of claim 1, further comprising receiving the aspect of the human user's physiological measurement data from a networked or non-networked peripheral device.

11. The system of claim 10, further comprising the peripheral device is any of a thermometer, pulse oximeter, blood pressure monitor, spirometer or a scale.

12. The system of claim 11, further comprising the peripheral device having a hardware processor.

13. The system of claim 1, further comprising determining and displaying a potential risk of an infectious disease.

14. The system of claim 13, further comprising displaying, in real-time, a warning of a potential risk of an infectious disease based on the multivariate analyses through supervised and unsupervised machine learning approaches.

15. The system of claim 14, further comprising the displaying including:
securely transmitting the human user's physiological measurement data and the survey answer using HIPAA-compliant AES-256 bit encryption;
accessing a cloud-based normative data storage having a normative data threshold, a risk ratio, and a recommendation;
comparing the human user's physiological measurement data to the normative data threshold and the risk ratio;
based on the comparison, determining a warning or an approval to enter a facility; and
transmitting the warning or the approval to enter the facility through the AES-256 bit encryption.

16. A method implemented on a hardware processor communicatively coupled to a mobile device having an application for displaying and transmitting of information from and to the hardware processor, the hardware processor executing instructions stored on a non-transitory media, the instructions for the method, the method comprising:
receiving a predetermined acceptable range for an aspect of a human user's physiological measurement data;
receiving a predetermined acceptable answer for a survey question; securely receiving an aspect of the human user's physiological measurement data;
determining if the aspect of the human user's physiological measurement data is within the predetermined acceptable range;
if the aspect of the human user's physiological measurement data is within the predetermined acceptable range, transmitting to the human user a survey comprising a question;
if the aspect of the human user's physiological measurement data is not within the predetermined acceptable range, transmitting an active alert comprising a warning of a potential risk of an infectious disease based on multivariate analyses and not providing the human user with the survey comprising the question;
if the human user fails to transmit an acceptable answer to the survey comprising the question, transmitting the active alert; and
presenting a display by the application on the mobile device in response to the human user's physiological measurement data being within the predetermined acceptable range and receiving the predetermined acceptable answer to the survey question from the human user, the display comprising a unique scannable code functioning as an electronically transferable access pass to an event or venue, the electronically transferable access pass being limited in transferability to other human users who have provided physiological measurement data within the predetermined acceptable range and who have further provided the predetermined acceptable answer to the survey question.

17. The method of claim 16, further comprising if the aspect of the human user's physiological measurement data is not within the predetermined acceptable range, transmitting infectious disease exposure risk survey questions to the human user.

18. The method of claim 16, further comprising receiving the aspect of the human user's physiological measurement data from a networked or non-networked peripheral device.

19. The method of claim 16, further comprising determining and displaying a potential risk of an infectious disease.

20. The method of claim 16, further comprising the display including:
- securely transmitting the human user's physiological measurement data and the survey answer using HIPAA-compliant AES-256 bit encryption;
- accessing a cloud-based normative data storage having a normative data threshold, a risk ratio, and a recommendation;
- comparing the human user's physiological measurement data to the normative data threshold and the risk ratio;
- based on the comparison, determining a warning or an approval to enter a facility; and
- transmitting the warning or the approval to enter the facility through the AES-256 bit encryption.

* * * * *